United States Patent [19]
Tei et al.

[11] Patent Number: 5,381,794
[45] Date of Patent: Jan. 17, 1995

[54] ULTRASONIC PROBE APPARATUS

[75] Inventors: Chuwa Tei, 25-3, Sakuragaoka 8-chome, Kagoshima-shi, Kagoshima-ken 890; Takashi Hosokawa, Mitaka; Tomoyuki Kato, Mitaka; Wataru Takekawa, Mitaka; Hisao Ito, Mitaka; Yoshihiro Yoshikawa, Mitaka, all of Japan

[73] Assignees: Aloka Co., Ltd.; Chuwa Tei, Japan

[21] Appl. No.: 7,346

[22] Filed: Jan. 21, 1993

[51] Int. Cl.⁶ .............................................. A61B 8/00
[52] U.S. Cl. .............................................. 128/662.03
[58] Field of Search ........................ 128/660.08–661.10, 128/662.03–662.06

[56] References Cited

U.S. PATENT DOCUMENTS

| | | | |
|---|---|---|---|
| 3,893,449 | 7/1975 | Lee et al. | 128/662.03 |
| 4,341,120 | 7/1982 | Anderson | 128/660.09 |
| 4,483,344 | 11/1984 | Atkov et al. | 128/662.03 |
| 4,947,853 | 8/1990 | Hon | 128/662.03 |
| 5,058,592 | 10/1991 | Whisler | 128/662.03 X |

FOREIGN PATENT DOCUMENTS

| | | |
|---|---|---|
| 0331348 | 2/1989 | European Pat. Off. . |
| 3709116 | 3/1987 | Germany . |
| 586405 | 8/1990 | Japan . |
| 2093188 | 2/1981 | United Kingdom . |

Primary Examiner—Francis Jaworski
Attorney, Agent, or Firm—Marger, Johnson, McCollom & Stolowitz

[57] ABSTRACT

An ultrasonic probe apparatus suitable for use in stress echocardiography testing is disclosed. This ultrasonic probe apparatus comprises, an ultrasonic probe provided with a phased array transducer for transmitting and receiving ultrasonic waves; a supporting member for supporting the ultrasonic probe rotationally and pivotally; and a plurality of deformable holding legs provided on the supporting member and formed of a copper plate coated with plastic so as to be able to be easily deformed by hand and further maintain its deformed state for a long time. Therefore, the ultrasonic probe apparatus can hold the ultrasonic probe stably onto a body surface of a person to be examined for a long time by appropriately deforming or bending any of the holding legs and then attaching the legs on the body surface in such a manner that the probe is in contact with the body surface, even if the body surface has various shape and unevenness. Further, the apparatus comprises a first motor for rotating the probe and a plurality of second motors for pivotally inclining the probe, so that the contact angle and direction of the probe with respect to the body surface of the examined person in exercise can be adjustably corrected or changed by remote control when the probe is dislocated or a scanning plane is required to be changed during the stress echocardiography testing.

25 Claims, 6 Drawing Sheets

ULTRASONIC PROBE APPARATUS

BACKGROUND OF THE INVENTION

1. Field of the Invention

The present invention relates to an ultrasonic probe apparatus, and more particularly to an ultrasonic probe apparatus which can hold an ultrasonic transducer assembly (hereinafter, referred to as "ultrasonic probe") having a phased array transducer in tight contact with a surface of an object to be examined.

2. Description of the Prior Art

In an ultrasonic diagnostic apparatus, ultrasonic waves are emitted from an ultrasonic transducer provided in an ultrasonic probe into an object to be examined. The echoes reflected from various parts of different acoustic impedances are received by the transducer, and data based on the received echoes are displayed on a cathode ray tube (CRT) as a visual image. In the ultrasonic diagnostic apparatus thus constructed, it is possible to observe properties of biological tissues of the object to be examined by displaying the obtained echo data as various tomographic images or by representing the echo data as dynamic curves (e.g. ultrasonic cardiograms).

In the conventional way of observing a tomographic image of a required region of a living body to be examined by means of the ultrasonic diagnostic apparatus, first an operator holds the ultrasonic probe with his hand, and then brings the transducer thereof into contact with the surface of the required region of the living body to be examined. Thereafter, the operator adjusts the contact angle and contact position of the probe with respect to the body surface appropriately, while observing the displayed image, in order to obtain a required ultrasonic tomographic image, for instance.

In recent years, an ultrasonic diagnostic method so called as stress echocardiography testing has been widely used. The stress echocardiography testing diagnoses a person to be examined through a B mode ultrasonic tomographic image under the condition that heart rate of the person is compellingly or forcibly increased by applying a load thereto. According to the stress echocardiography testing, it is possible to observe cardiac function of a person to be examined which can not be observed under the condition that the person is lying quiet in bed, which is advantageous in finding an early stage of a heart disease such as ischemic heart disease (IHD).

As the methods performing the stress echocardiography testing, there are known some methods. In these methods, there is a method in which medicine or electrical shock is given to a person to be examined in order to compellingly increase its heart rate. However, this method has problems due to less safety for the examined person or increased burden of the examined person. For these reasons, there is widely used a method in which a person to be examined is exercised under the natural condition by using a treadmill or the like to increase its heart rate compellingly and cardiac function of the heart of the person under that condition is observed through B mode ultrasonic tomographic image.

The above method is preferable in view of the safety and reduced burden of the examined person. However, in this method, a diagnosis has to be performed under the condition that the examined person is walking or running on the treadmill with standing posture, which is quite different from the condition that the person is lying quiet in bed. Further, in the stress echocardiography testing, it is required to obtain data on the same part of the examined person for several times over a relatively long time, for example at three minutes after, five minutes after and ten minutes after.

Therefore, in the stress echocardiography testing, is required to accurately maintain the probe for a long time at a predetermined position on the body surface of the examined person who is walking or running with standing posture. Therefore, in the conventional method, two operators are required to attend the stress echocardiography testing, in which one of the operators holds the probe with his hand on the body surface of the examined person and the other operator manipulates and monitors the diagnostic apparatus.

However, the prior art method is not economical because two operators are required to attend the diagnosis. Further, it is difficult to obtain an accurate B mode ultrasonic tomographic image by merely holding the ultrasonic probe with the hand of the operator since the scanning plane is likely to be dislocated during the diagnosis by the vibration from the examined person. For these reasons, it has been desired to develop an apparatus which is suitable for use in the stress echocardiography testing, that is an apparatus which can hold the ultrasonic probe stably on the body surface of the examined person for a long time during the stress echocardiography testing.

As such an apparatus that can hold an ultrasonic probe onto a body surface of the examined person, there is known one which is disclosed in Japanese Utility Model Publication No. 58-6405.

Figure 1:
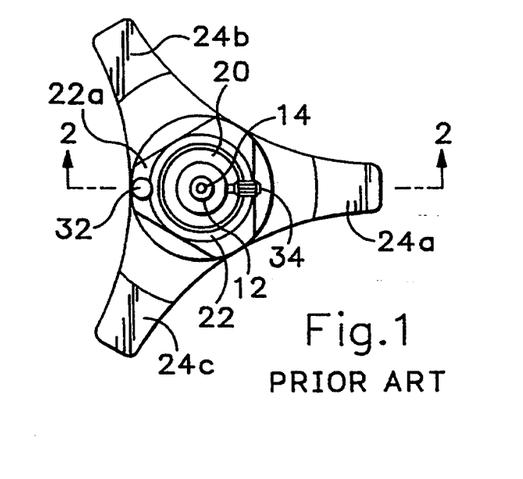
FIG. 1 is a plan view showing a prior art ultrasonic probe apparatus.
Figure 2:
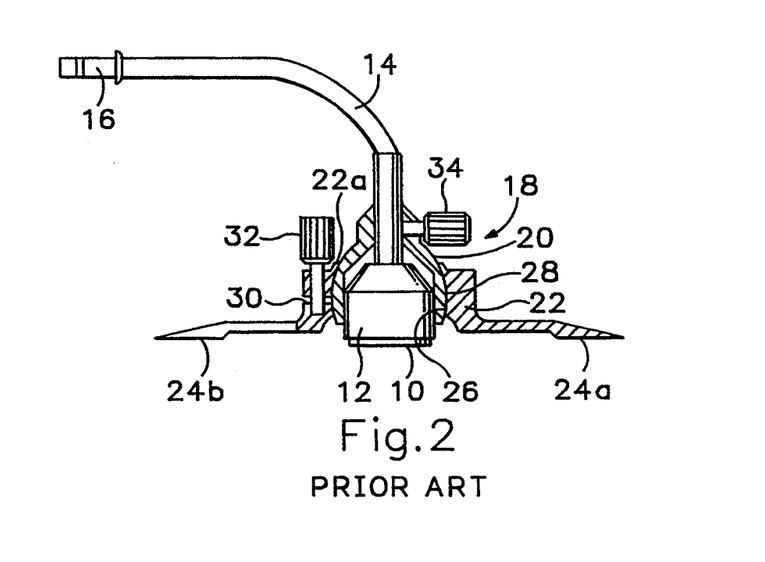
FIG. 2 is a cross-sectional view showing the same prior art ultrasonic probe apparatus, taken along the line 2—2 in FIG. 1.

FIGS. 1 and 2 show the ultrasonic probe apparatus disclosed in this Utility Model Publication. The apparatus comprises a roughly cylindrical ultrasonic probe 12 provided with a single element ultrasonic transducer 10 for emitting and receiving an ultrasonic beam, and a supporting member 18 for supporting the ultrasonic probe 12 so as to be pivotable and inclinable.

Further, a cable 14 is connected to the ultrasonic probe 12, in order to transmit a signal for exciting the ultrasonic transducer 10 from a control section off an ultrasonic diagnostic apparatus (not shown) to the transducer 10 and feed an echo signal based on the echo received by the ultrasonic transducer 10 to the control section of the diagnostic apparatus. Further, a male connector 16 to be coupled to a female connector (not shown) of the control section of the ultrasonic diagnostic apparatus is attached to a free end of the cable 14.

The supporting member 18 includes a first holder 20 for supporting the ultrasonic probe 12 therewithin and a second holder 22 for supporting the first holder 20 which supports the probe 12 so as to be pivotable and inclinable with respect to the second holder 22.

The first holder 20 is formed into a roughly semispherical shape having an inner space into which the ultrasonic transducer assembly 12 can be fitted. The cable 14 extends from the top of the first holder 20. The ultrasonic probe 12 fitted into the inner space of the first holder 20 is adjustably pivoted and then fixed therein with a locking screw 34. Further, when this locking screw 34 is loosened, the ultrasonic probe 12 can be removed from the first holder 20 so as to be usable for the ordinary ultrasonic diagnosis.

The second holder 22 is provided with a cylindrical portion 22a having an opening to which the first holder 20 can be fitted. The inner circumferential surface of this cylindrical portion 22a is formed into a semi-spherical surface which defines a pivotal holding portion 26, to which a semi-spherical pivotal portion 28 defined by an outer spherical circumferential surface of the first holder 20 is pivotally fitted. Accordingly, the ultrasonic probe 12 can be held pivotally relative to the second holder 22 of the supporting member 18 through the first holder 20.

Further, a slit 30 is formed at a part of the cylindrical portion 22a of the second holder 22, so as to extend radially to the inner opening thereof in the horizontal direction perpendicular to the axial direction of the cylindrical portion 22a. A threaded hole is formed at the part of the cylindrical portion 22a in which the slit 30 is formed, so as to pass through The slit 30 in the axial direction of the cylindrical portion 22a. Into this threaded hole, a locking screw 32 is screwed, so that both the holders 20 and 22 can be fixed with respect to each other when the locking screw 32 is fastened.

The second holder 22 is formed integrally with three holding legs 24a, 24b and 24c. These legs 24a, 24b and 24c are formed of a relatively hard material and extend radially outward in the direction perpendicular to the axial direction of the cylindrical portion 22a at regular angular intervals. Therefore, the ultrasonic probe 12 can be held onto a body surface of a person to be examined in such a manner that the transducer 10 is brought into contact with the body surface, when these legs 24a, 24b and 24c are attached onto the body surface by use of an adhesive tape, for instance.

In use of this prior art ultrasonic probe apparatus constructed as described above, first the ultrasonic probe 12 is mounted within the first holder 20 with a locking screw 34. Thereafter, the first holder 20 with the probe 12 is mounted to the second holder 22 by means of the locking screw 32. Further, the three holding legs 24a, 24b and 24c are attached onto the body surface of the person to be examined with an adhesive tape in such a manner that the ultrasonic transducer 10 is brought into tight contact with the body surface. Under these conditions, an ultrasonic beam is emitted from the ultrasonic transducer 10 arranged inside the ultrasonic probe 12 toward a required biological tissue to be examined through the body surface, and the echo reflected from the biological tissue is received by the transducer 10.

This prior art ultrasonic probe apparatus has been developed mainly for use in ultrasonic cardiography testing for a person to be examined who is lying quiet, in bed. However, if this prior art ultrasonic probe apparatus would be applied to stress echocardiography testing, it is supposed that the desire described above that holds the ultrasonic probe onto the body surface of the examined person for a long time during the stress echocardiography testing may be satisfied.

However, in this prior art ultrasonic probe apparatus, since the holding legs 24a, 24b and 24c integrally formed with the second holder 22 do not have flexibility, there is a case that these legs 24a, 24b and 24c are not sufficiently attached to the body surface due to the difference in a figure of a body of individual person to be examined. In particular, during the stress echocardiography testing, the examined person is sometimes imposed to have unnatural posture in which a body surface thereof is deformed.

Further, in diagnosis for ischemic heart disease (IHD), it is necessary to obtain a tomographic image of a heart along a minor axis direction thereof. In obtaining such a tomographic image, the ultrasonic probe apparatus has to be attached onto a body surface of a person to be examined at a position just below the left ribs thereof such that the beam from the transducer is directed upwardly. However, there are many unevenness such as ribs or breast around that position. Therefore, it is difficult to attach and hold the prior art ultrasonic transducer apparatus on that position appropriately and stably.

For these reasons, the prior art ultrasonic probe apparatus can not be used in the stress echocardiography testing as it is.

Furthermore, during the stress echocardiography testing, there is a case that different regions of the heart are required to be diagnosed, or that the scanning plane by the transducer is dislocated due to the motion or the vibration of the examined person. Therefore, in the ultrasonic transducer apparatus for the stress echocardiography testing, it is preferable that the ultrasonic wave emitting direction can be adjusted under the fixed condition by modifying or correcting the contact angle and contact position of the ultrasonic probe relative to the examined person, if necessary. In addition, in order to obtain a preferable B mode tomographic image, it is necessary to adjust the ultrasonic wave emitting direction appropriately under the fixed condition. However, it is difficult to satisfy these necessities by merely applying the prior art ultrasonic transducer apparatus to the stress echocardiography testing.

SUMMARY OF THE INVENTION

With these problems in mind, therefore, it is a primary object of the present invention to provide an ultrasonic probe apparatus suitable for use in stress echocardiography testing, which can hold an ultrasonic probe stably on a body surface of a person to be examined for a long time, irrespective of various figures of persons.

Further, it is the other object of the present invention to provide an ultrasonic probe apparatus which can correct the ultrasonic wave emitting direction by means of remote control, in case the ultrasonic wave emitting direction is dislocated during diagnosis.

In order to achieve the above-mentioned primary object, the ultrasonic probe apparatus according to the present invention comprises, an ultrasonic probe provided with a phased array transducer for transmitting and receiving ultrasonic waves; means for supporting the ultrasonic probe rotationally and pivotally; and means for holding said supporting means which supports said ultrasonic probe on a surface of an object to be examined, the holding means being adapted to be freely deformable according to a figure of the object to be examined and further retainable in the deformed state.

In the ultrasonic probe apparatus according to the present invention, since the holding means is freely deformable according to the figure of the object to be examined, and additionally can be retained in the deformed state, it is possible to deform the holding means appropriately so as to conform to the figure of a person to be examined. In addition, the deformed state can be retained for many hours. As a result, it is possible to locate and hold the ultrasonic probe on a body surface of an examined person at any required position for a long time during the stress echocardiography testing.

The holding means is preferably composed of a plurality of holding legs provided on the supporting means and extending radially outward. Each of these holding legs can be made from a metal plate coated with a polymer. Preferably, the metal plate is formed of a copper.

Further, in order to achieve the other above-mentioned object, the ultrasonic probe apparatus according to the present invention comprises an ultrasonic probe provided with a phased array transducer for transmitting and receiving ultrasonic waves; means for supporting the ultrasonic probe rotationally and pivotally; means for holding said supporting means which supports said ultrasonic probe on a surface of an object to be examined; and means for shifting said ultrasonic probe in any desired directions by remote control under the condition that the ultrasonic probe is held on the surface of the object to be examined.

In the above-mentioned ultrasonic probe apparatus according to the present invention, since the angle and direction of the ultrasonic probe with respect to the examined person can be adjustably corrected or changed by remote control shifting means, dislocation can be corrected when such dislocation has been caused or a scanning plane can be changed when a different region is required to be diagnosed during the diagnosis.

The shifting means can be constructed from means for rotating and pivotally inclining the ultrasonic probe with respect to the supporting means. The rotating means comprises preferably a motor for rotating the ultrasonic probe provided on the supporting means and other motors for pivotally inclining the ultrasonic probe provided on the supporting means.

The other objects, structures and advantages of the present invention will be apparent from the following description of the preferred embodiment of the present invention with reference to the attached drawings.

DETAILED DESCRIPTION OF THE PREFERRED EMBODIMENTS

A preferred embodiment of the ultrasonic probe apparatus according to the present invention will be described hereinbelow with reference to the attached drawings, in which the same reference numerals denote similar parts or elements which have the same functions as those in the prior art apparatus previously described with reference to FIGS. 1 and 2.

Figure 3:
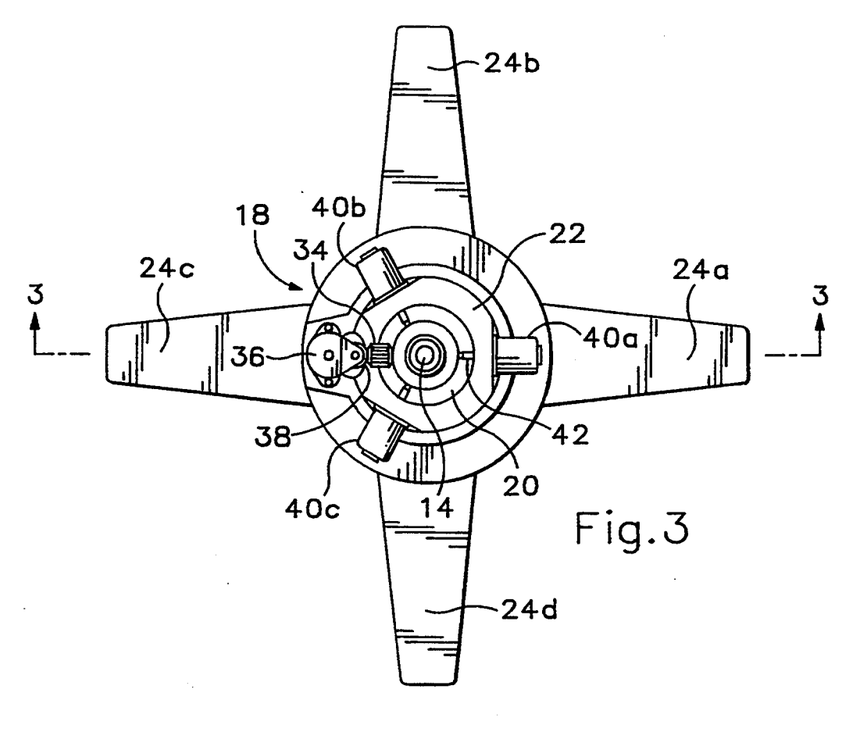
FIG. 3 is a plan view showing an ultrasonic probe apparatus according to the present invention.
Figure 4:
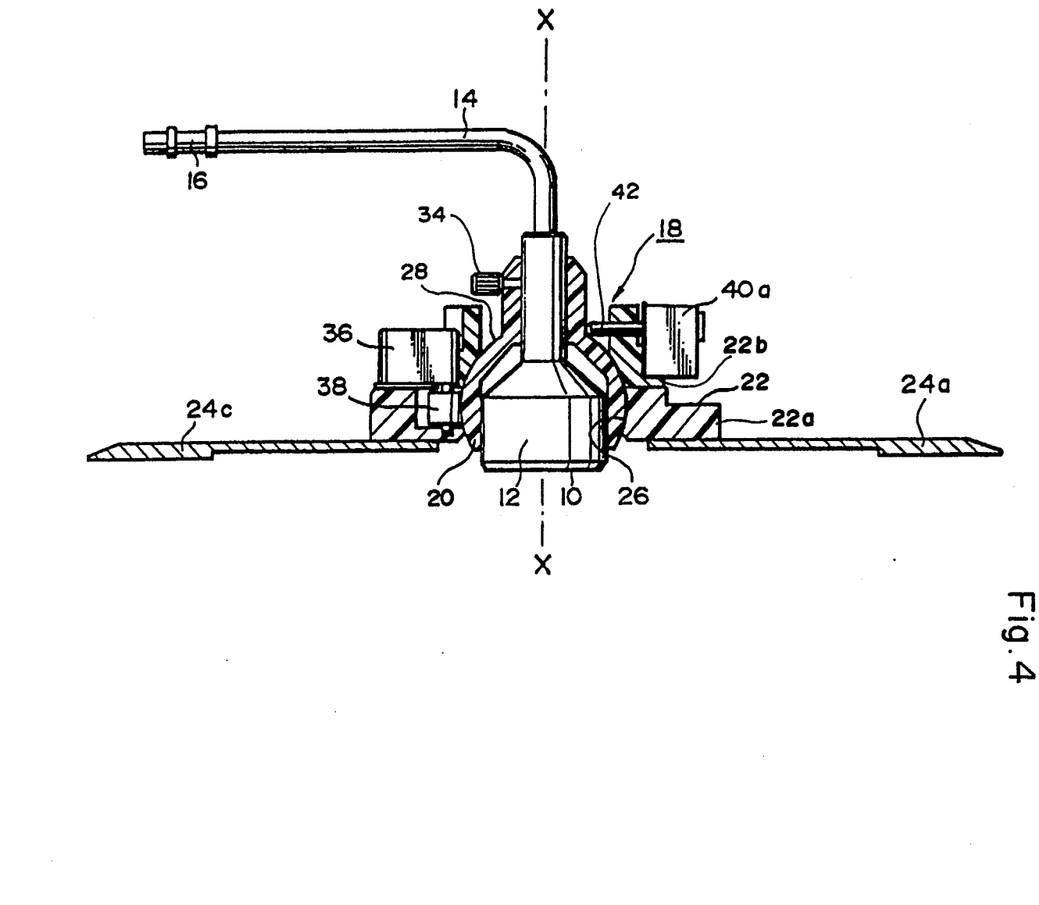
FIG. 4 is a cross-sectional view showing the same ultrasonic probe apparatus according to the present invention, taken along the line 3—3 shown in FIG. 3.

As shown in FIGS. 3 and 4, the ultrasonic probe apparatus of the embodiment comprises an ultrasonic probe 12 formed into a roughly cylindrical shape and provided with a phased array ultrasonic transducer 10 for transmitting and receiving ultrasonic waves therewithin, and a supporting member 18 for supporting the ultrasonic probe 12 so as to be rotatable and pivotal. That is, the ultrasonic probe 12 is supported by the supporting member 18 in such a way that the ultrasonic probe 12 is rotatable about the central axis X thereof and further the central axis X is freely pivotal and inclinable relative to the supporting member 18.

A cable 14 is connected to the ultrasonic probe 12 to transmit exciting signals from a control section of an ultrasonic diagnostic apparatus (not shown) to the ultrasonic transducer 10 and feed echo signals based on the echoes received by the same transducer 10 to the control section of the diagnostic apparatus. A male connector 16 to be coupled to a female connector provided on the control section of the ultrasonic diagnostic apparatus is attached to the free end of the cable 14. Further, the phased array ultrasonic transducer 10 is arranged within the probe 12 on and along the end surface thereof.

The supporting member 18 comprises a first holder 20 for supporting the ultrasonic probe 12 therewithin such that the ultrasonic probe 12 is pivotal together with the first holder 20, and a second holder 22 for rotatably and pivotally supporting the first holder 20 in which the probe 12 is fitted.

Specifically, the first holder 20 is constituted from a roughly semi-spherical portion having an open end and a cylindrical portion integrally connected to the semi-spherical portion, in which inner space to which the ultrasonic probe 12 is fitted is defined. On the cylindrical portion, there is provided a screw 34 for adjusting the position of the probe 12 with respect to holder 20 in the axial direction of the probe 12. The cable 14 extends from the top of cylindrical portion of the first holder 20.

The second holder 22 is formed from a roughly cylindrical lower annular portion 22a, and an upper annular portion 22b provided on the lower annular portion 22a and having an outer diameter smaller than that of the lower annular portion 22a. The central portions of these annular portions 22a and 22b are open in the axial direction thereof. The inner circumferential surfaces of these upper and lower annular portions 22a and 22b which define the opening are formed into roughly a semi-spherical surface, respectively so as to provide a pivotal holding portion 26. To this pivotal holding portion 26, another pivotal portion 28 defined by a semi-spherical outer surface of the first holder 20 is pivotally fitted, so that the first holder 20 which supports the ultrasonic probe 12 therein can be rotated and pivoted freely relative to the second holder 22 of the supporting member 18.

Further, on the lower side of the lower annular portion 22a of the second holder 22, there are fixed four narrow and elongated holding legs 24a, 24b, 24c and 24d extending radially outward in the direction perpendicular to the axial line of the annular portion 22a in X-shape at regular angular intervals (90-degree intervals).

Figure 5:
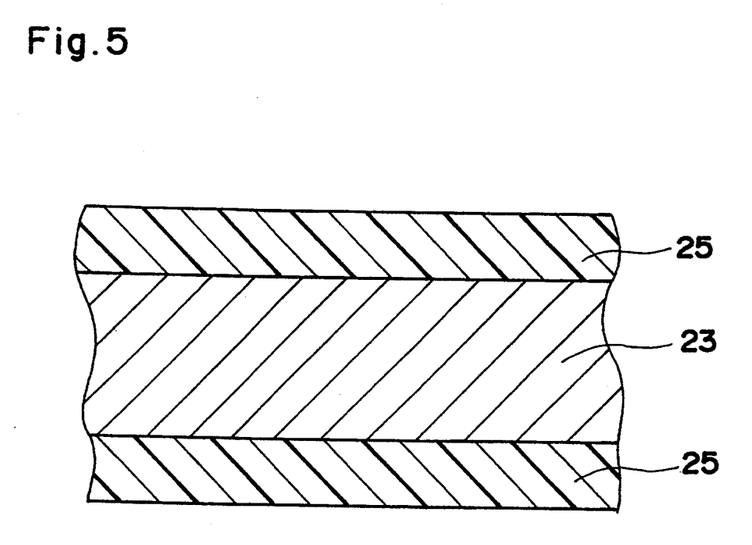
FIG. 5 is an enlarged cross-sectional view which shows an example of the holding leg.

These holding legs 24a, 24b, 24c and 24d are formed of a material freely deformable and further retainable in the deformed state for a long time. Preferably, these holding legs 24a, 24b, 24c and 24d are formed of a metallic material having such a flexural rigidity (generally determined by thickness and material thereof) that can be easily plastically-deformed by hand of a person, for instance. More preferably, as shown in FIG. 5, these legs are formed from a metallic material 23 oil which at least one coating layer is formed.

As the metallic material described above, for example, copper, oxygen free copper, copper alloy such as phosphor bronze or brass, soft steel, ferro-alloy such as stainless steel, aluminum, lead, tin or zinc can be used. In these materials, copper, copper alloy and soft steel are preferable in view of their availability, and oxygen free copper, phosphor bronze and stainless steel are preferable in view of their corrosion resistance ability. Further, on the surface of the metallic material, surface treatment may be applied by forming a plating layer such as a choromium, zinc, thin or alloy of these materials for the purpose of improvement of corrosion resistance ability or adhesivity of the coating layer.

Further, these legs 24a, 24b, 24c and 24d can be formed of a material in which more than two metal plates are stacked with each other like a bimetal. In this case, as the metallic material for each metal plate, the above described metallic materials can be selectively used. Further, a layer formed of a synthetic resin can be sandwiched between the metallic plates. According to the holding legs formed from layered materials as described above, it is possible to possess the characteristics of each material forming each layer and to easily change the flexural rigidity of the legs by appropriately adopting the materials to be combined.

Here, it should be noted that the metallic materials for forming the holding legs 24a, 24b, 24c and 24d are not limited to the metallic materials described above. Any other metallic materials can be used if the materials have such a flexural rigidity that is easily plastically deformed by hand of a person.

Furthermore, as the metallic materials forming the holding legs 24a, 24b, 24c and 24d, it is possible to use a shape memory alloy which has a characteristic that restores into its initial shape having a flat configuration as shown in FIG. 4 under the ordinary temperature. In a case where such a shape memory alloy is used as the material forming the legs, adjustment of bending angle of each leg can be made easily when the same ultrasonic transducer apparatus is used in order to diagnose a different part of the same examined person or a different person to be examined, since each of the holding legs can always keep a flat shape when used.

As the thickness of the metallic material which forms the holding legs 24a, 24b, 24c and 24d, if a copper plate is adopted as the material, the thickness thereof is preferably set to 0.2 mm–1.0 mm, and more preferably set to 0.4 mm–0.8 mm, although this would be changed depending on the width thereof.

As stated in the above, the coating layer 25 is formed onto the metallic material 23, of which purposes are as follows:

(1) Preventing the metallic material from being corroded or altered.
(2) Cutting off elusion of metallic ion from the metallic material.
(3) Preventing skin from being injured by an edge of the metallic material, thereby improving safety.
(4) Moderating shock which would be occurred by the temperature difference between the skin and the legs when the legs contact with the skin.
(5) Buffering physical shock which would be occurred when the legs abut with the skin.
(6) Securing insulation between the legs and the skin.
(7) Increasing frictional force between the legs and the skin, thereby improving stability of the legs to the skin.

In view of some of these purposes for forming the coating layer 25, appropriate materials for the coating layer 25 and appropriate thickness thereof can be chosen.

As the materials for forming the coating layer 25, various polymers can be used. For example, soft polyvinyl chloride; medical unplasticized polyvinyl chloride; polyolefine such as polyethylene, polypropylene, polybutadiene or ethylene-vinil acetate copolymer; aromatic or aliphatic polyamide; polyimide; polyvinylidene chloride; polyvinyl alcohol; polyeurethane; fluoro rubber: natural rubber; isoprene rubber; latex rubber; silicone material such as silicone rubber; or materials formed by polymer blend of some of these polymers mentioned above can be used. In these polymers, medical unplasticized polyvinyl chloride and silicone materials are especially preferable in view of less influence to human body.

Figure 6:
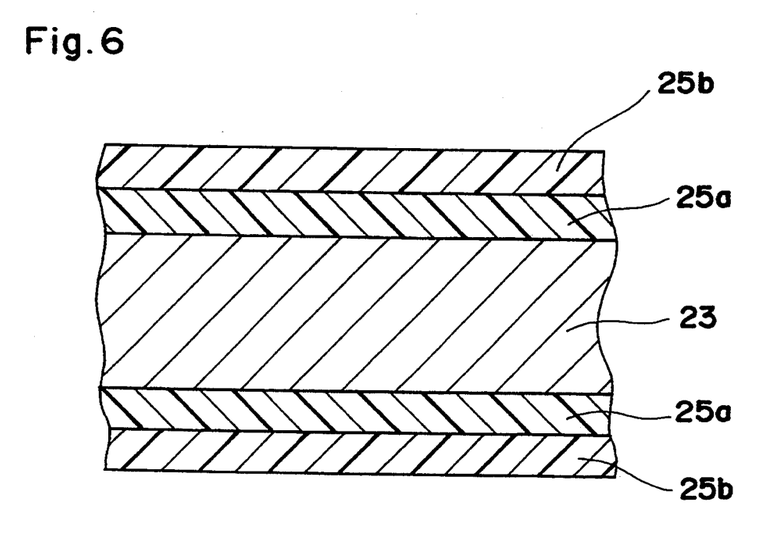
FIG. 6 is an enlarged cross-sectional view which shows another example of the holding leg.

Further, as shown in FIG. 6, it is possible to form a plurality of layers such as coating layers 25a and 25b on the metallic material 23. As the materials which form respective coating layers 25a and 25b, any of the above mentioned polymers can be selectively used. If the coating layer 25 is formed from more than two layers, it becomes possible to enjoy respective characteristics of the materials which form the layers and any of the purposes described above can be attained by adopting materials to be combined appropriately.

The coating layer 25 can be formed only on a tip part of each of the legs 24a, 24b, 24c and 24d which abuts the skin when the apparatus is attached to the body surface of the person to be examined. However, it is preferable to form the coating layer 25 so as to cover the entire of each holding leg.

The total thickness of the coating layer 25 is preferably set to 0.1 mm–3.0 mm and more preferably to 0.5 mm–1.5 mm, although it depends on the purpose for forming the coating layer and the material from which the coating layer is formed.

In this embodiment, it should be noted that it is possible to construct the holding legs 24a, 24b, 24c and 24d such that each of the legs has different structural factors such as dimension (length, width and thickness), a material which forms the leg, a position at which the coating layer is applied, the number of the layers, a material which forms the coating layer 25 and thickness of the coating layer. Of course, it is possible for the holding legs to have the same structural factors. If these legs have the same structural factors, assembly operation of the apparatus and attachment operation of the apparatus to a body surface of a person to be examined can be made easily, since it is possible to disregard the direction of the legs.

By deforming each of the legs appropriately so as to conform with the shape of the body surface of the person to be examined, the ultrasonic probe apparatus can be attached to an uneven part of the body such as a position just below ribs or below breast. In this case, since the ultrasonic probe apparatus has four holding legs constituted as described above, it becomes possible to hold the ultrasonic probe apparatus stably onto the body surface by using any three of the holding legs even when one of the legs can not contact with the body surface due to a position to which the apparatus is attached.

Thereafter, by attaching the legs 24a, 24b, 24c and 24d which have been deformed into required shapes onto the body surface by means of adhesive agent, adhesive tape or fastening belts or the like, it is possible to hold the ultrasonic probe apparatus on the body surface of the person to be examined stably.

In the most preferable example, the four holding legs 24a, 24b, 24c and 24d are formed from a copper plate, each of which has the length of 60 mm, the width of 10 mm and the thickness of 0.3 mm. Further, on the surface of each of the copper plates, a coating layer formed of medical unplasticized polyvinyl chloride or silicone rubber is applied. By use of thus formed holding legs, the ultrasonic probe apparatus is assembled. Thus assembled apparatus is attached to the body surface of the examined person at a position below the ribs thereof by bending and deforming each of the legs into appropriate configurations and then attaching these deformed legs onto the body surface by means of an adhesive tape. In this example, there is no uncomfortableness to the examined person when the holding legs are attached to the body surface. Further, each of the legs can keep its deformed configuration during the exercise of the examined person and no dislocation is caused between the apparatus and the body surface.

Turning now back to the other structure of the ultrasonic probe apparatus, in the second holder 22, there are provided a rotational motion motor 36 for rotating the first holder 20 in which the ultrasonic probe 12 is fitted, with respect to the second holder 22; and three inclination motion motors 40a, 40b and 40c for pivotally inclining the first holder 20 with respect to the second holder 22.

The rotational motion motor 36 is disposed on the lower annular portion 22a of the second holder 22 in such a way that a rotary shaft thereof is in parallel to the axial line of the annular portion 22a. A roller 38 is attached to the rotary shaft of this motor 36 so as to be brought into contact with the outer circumferential surface of the first holder 20, so that the rotational motion motor 38 can rotate the first holder 20 within an angular range between +90 and −90 degrees.

On the other hand, the three inclination motion motors 40a, 40b and 40c are disposed on the upper annular portion 22b of the second holder 22 at regular angular intervals (120-degree intervals) along the circumferencial direction thereof. The rotary shafts of these motors 40 are directed in the horizontal direction, that is, extending radially outward in the direction roughly perpendicular to the axial line of the annular portions 22a, 22b. A rod 42 movable in and out in the radial direction of the annular portion 22a is screw-engaged with each of the rotary shafts of the motors 40, so that each of the movable rods 42 can be moved in and out horizontally by the rotation of each motor 40a, 40b, 40c, respectively. The movable rods 42 are disposed so as to pass through the upper annular portion 22b and contact with the upper portion of the first holder 20 fitted to the inner opening of the annular portion 22b, respectively. These movable rods 42 are freely movable in and out relative to the second holder 22, respectively, when rotated by the motors 40, respectively. Therefore, it is possible to freely incline or pivot the first holder 20 with respect to the second holder 22 by driving any one of the motors 40a, 40b and 40c to change the direction of the probe 12 appropriately.

Further, although not shown, conductive wires for supplying driving currents to the rotational motion motor 36 and the inclination motion motors 40a, 40b and 40c are all connected to the control section of the ultrasonic diagnostic apparatus through the cable 14 connected to the ultrasonic transducer 10.

The operation of the apparatus according to the above described embodiment will be described hereinbelow.

In a case where the cardiac function of a heart of a person to be examined to which a load is being applied is required to be observed by the ultrasonic diagnostic apparatus which uses the ultrasonic probe apparatus, first the ultrasonic probe 12 is removed from the supporting member 18 by loosening the screw 34 and then the supporting member 18 is displaced upwardly relative to the ultrasonic probe 12 along the cable 14. Under the condition, the operator holds the probe 12 with his hand and then brings it into contact with the body surface of the examined person and adjusts the contact position with monitoring the CRT in order to locate a region at which an appropriate B mode image can be obtained.

Figure 7:
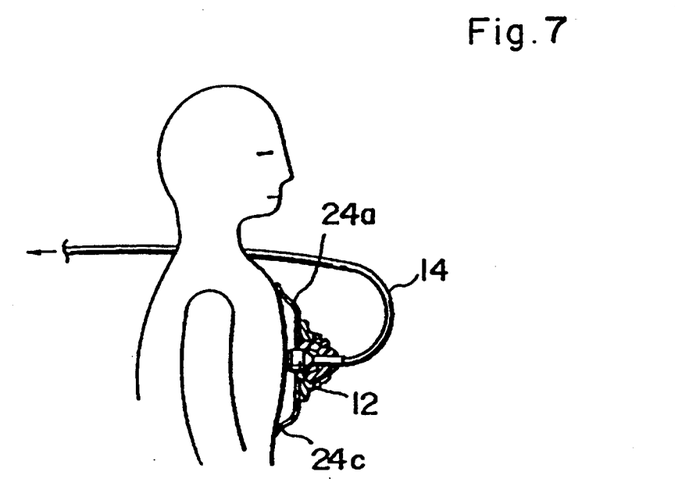
FIG. 7 is an illustration showing the state where the ultrasonic probe apparatus according to the present invention is attached to a body to be examined.

When the appropriate position can be located, the supporting member 18 is mounted to the ultrasonic probe 12 by fastening the screw 34 under the condition that the probe 12 is positionally maintained at the appropriate position. In this state, the respective holding legs 24a, 24b, 24c and 24d are appropriately bent or deformed such that the transducer 10 of the probe 12 which has been mounted to the supporting member 18 can be kept in contact with the body surface at the appropriate position. Thereafter, the holding legs 24a, 24b, 24c and 24d are attached to the body surface by use of an adhesive tape or the like, so that the ultrasonic probe apparatus is fixed onto the body surface in such a manner that the probe 12 is in contact with the body surface, as shown in FIG. 7.

Figure 8:
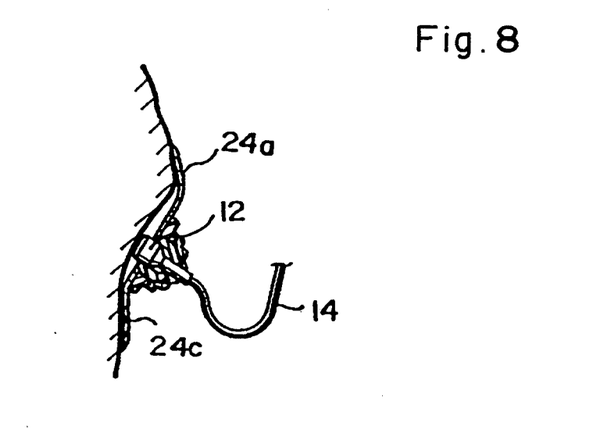
FIG. 8 is an illustration showing the state where the ultrasonic probe apparatus according to the present invention is attached to an uneven part of a body to be examined.

Further, if the body surface is not even, as shown in FIG. 8, the respective holding legs 24a, 24b, 24c and 24d are further bent or deformed appropriately so that the transducer 10 of the ultrasonic probe 12 can be brought into tight contact with the body surface at the appropriate position. In this case, the mounting position of the probe 12 with respect to the first holder 20 of the supporting member 18 in the axial direction thereof can be adjusted by use of the screw 34 in order that the probe 20 is brought into contact with the body surface appropriately.

Therefore, in the ultrasonic probe apparatus according to the present invention, since the holding legs 24a, 24b, 24c and 24d can be appropriately adjusted according to the figure of the body to be examined (e.g. the degrees of physique, corpulence, stature, etc. caused by differences between individuals), it is possible to hold the ultrasonic probe 12 tightly on the body surface under a stable condition even if there is unevenness therearound. In addition, since the bent or deformed holding legs 24a, 24b, 24c and 24d can be retained in the deformed state for a long time due to their material characteristics, the ultrasonic probe 12 is kept fixed tightly on the body surface of the examined person during a long-time diagnosis.

Figure 9:
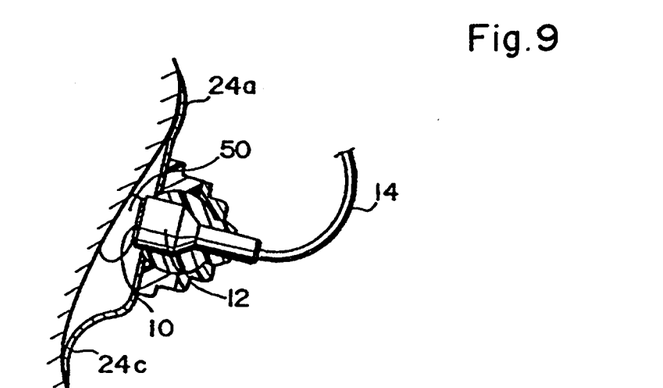
FIG. 9 is an illustration showing the state where an ultrasonic propagating medium is interposed between the ultrasonic probe apparatus according to the present invention and the uneven part of the body to be examined.

Furthermore, it is preferable to interpose an appropriate gel-state acoustic propagation medium 50 between the ultrasonic transducer 10 and the body surface, as shown in FIG. 9.

After the ultrasonic probe apparatus has been attached to the body surface, a load is applied to the examined person by compelling him to walk or run on a treadmill, for instance. Under these conditions, exciting signals are supplied from the control section of the ultrasonic diagnostic apparatus to the ultrasonic transducer 10 through the connector 16 and cable 14 to emit ultrasonic waves from the transducer 10 to a diagnosed part of the examined person. The echoes reflected from parts having different acoustic impedances of the examined body are received by the same ultrasonic transducer 10 to display a tomographic image of a heart, for instance on a display unit (e.g. CRT) on the basis of the obtained echo signals.

Further, there exists a case where the ultrasonic probe apparatus is dislocated due to vibration for instance from the examined person in exercise, and therefore the direction in which the ultrasonic waves are emitted from the transducer 10 changes from the original direction determined before the diagnosis. In this case, however, the operator can correct the direction of the probe 12 to any given direction so that the ultrasonic waves can be emitted toward any required region (e.g. the direction in which a tomographic image of a heart can be obtained along the heart minor axis), by remote control; that is, by rotating the rotational motion motor 36 and any one of the inclination motion motors 40a, 40b and 40c clockwise or counterclockwise, while watching a heart tomographic image now being displayed on the CRT. As described above, it is possible to determine the ultrasonic scanning plane freely and easily to any desired directions, by operating the ultrasonic probe apparatus of the present invention.

Figure 10:
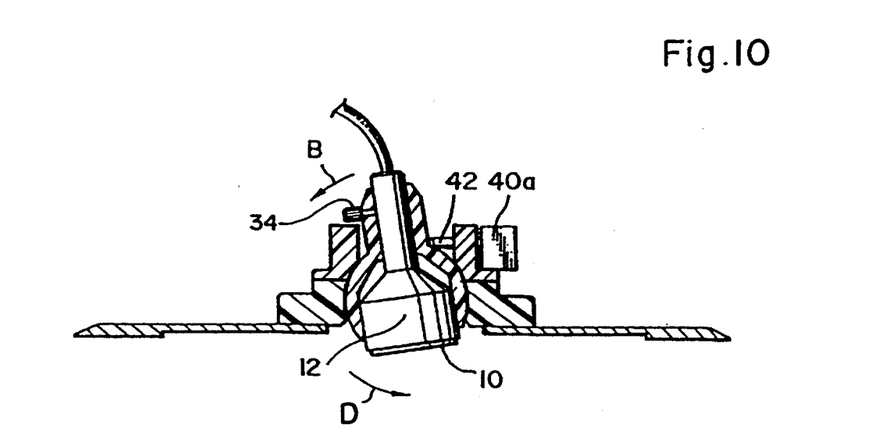
FIG. 10 is a cross-sectional view for assistance in explaining the movement of the ultrasonic probe in the ultrasonic probe apparatus according to the present invention.

Further, as shown in FIG. 10, when the inclination motion motor 40a is activated by remote control operation, the movable rod 42 is shifted horizontally leftward in the drawing to push the first holder 20, so that the first holder 20 is pivoted in the counterclockwise direction D via the coupling surfaces 26, 28 between the first and second holders 20 and 22. As described above, it is also possible to incline the ultrasonic probe 12 in any directions by driving a single or a plurality of the inclination motion motors 40.

In addition, when the rotational motion motor 36 is driven by the remote control operation, since the heart tomographic image can be rotated clockwise or counterclockwise within the range from +90 to −90 degrees, it is also possible to obtain tomographic images at any required regions.

In the ultrasonic probe apparatus according to the present invention, there exist such advantages that the ultrasonic probe 12 can be not only securely located and fixed to a body surface of an examined person who is walking or running on a treadmill, but also the direction of the located ultrasonic probe 12 with respect to the body surface of the examined person can be adjustably corrected or changed during the stress echocardiography testing, according to the necessity.

In the above described embodiment of the present invention, a probe having a phased array transducer for B mode ultrasonic diagnosis is used. However, it is of course possible to use a probe which can perform M mode ultrasonic diagnosis or ultrasonic Doppler method diagnosis instead of such a probe described above.

Finally, it should be noted that the above-mentioned embodiment of the ultrasonic probe apparatus according to the present invention has been explained only by way of example. Therefore, the scope of the present invention is not limited to the embodiment, but defined by the appended claims.

What is claimed is:

1. An ultrasonic probe apparatus comprising:
   an ultrasonic probe provided with a phased array transducer for transmitting and receiving ultrasonic waves;
   means for supporting said ultrasonic probe rotatably and pivotally; and
   means for holding said supporting means which supports said ultrasonic probe on a body surface of an object to be examined in such a manner that ultrasonic beams transmitted from the transducer of the probe are directed to a region in the body to be diagnosed,
   said holding means including a plurality of elongated holding legs coupled to said supporting means so as to extend therefrom radially and outwardly with respect to a rotation axis of the probe and adapted to maintain direct contact with the body surface,
   said holding legs being adapted to be freely deformable according to a profile of the object to be examined and further retainable in the deformed state, and said holding legs adapted to be attached to the body surface with fixing means such as an adhesive tape so that said probe is held onto the body surface irrespective of the profile of the object to be examined, the ultrasonic beams from said probe directed to the region to be diagnosed by appropriately deforming the holding legs to meet with the profile of the object to be examined.

2. The ultrasonic probe apparatus of claim 1, wherein each of said holding legs is formed of a metallic material having such a flexural rigidity that could be easily plastically-deformed.

3. The ultrasonic probe apparatus of claim 2, wherein the metallic material is a copper.

4. The ultrasonic probe apparatus of claim 2, wherein at least one coating layer formed of polymer is provided on the surface of the metallic material.

5. The ultrasonic probe apparatus of claim 4, wherein the coating layer is formed over the entire of each leg.

6. The ultrasonic probe apparatus of claim 4, wherein the coating layer is formed of medical unplasticized polyvinyl chloride.

7. The ultrasonic probe apparatus of claim 4, wherein the coating layer is formed of silicone materials.

8. The ultrasonic probe apparatus of claim 2, wherein said supporting member has a lower part, and the plurality of holding legs includes four holding legs fixed in an X-shape configuration extending radially around the lower part of the supporting member, and each of the legs formed into a fiat plate-like configuration having a narrow width.

9. The ultrasonic probe apparatus of claim 1, wherein said supporting member comprises a first holder for supporting said ultrasonic probe therewithin, and a second holder for rotatably and pivotally supporting said first holder.

10. The ultrasonic probe apparatus of claim 9, further comprising means for shifting said ultrasonic probe in any desired directions by remote control under the condition that said probe is held on the surface of the object to be examined.

11. The ultrasonic probe apparatus of claim 10, wherein said ultrasonic probe shifting means comprises means for rotating said first holder relative to said second holder, and means for pivoting or inclining said first holder relative to said second holder.

12. An ultrasonic probe apparatus comprising:
an ultrasonic probe provided with a phased array transducer for transmitting and receiving ultrasonic waves;
means for supporting said ultrasonic probe rotatably and pivotally including a first holder for supporting said ultrasonic probe therewithin, and a second holder for rotatably and pivotally supporting said first holder; and
means for holding said supporting means which supports said ultrasonic probe on a surface of an object to be examined, said holding means being adapted to be freely deformable according to a figure of the object to be examined and further retainable in the deformed state;
means for shifting said ultrasonic probe in any desired direction by remote control under the condition that said probe is held on the surface of the object to be examined, said ultrasonic probe shifting means including a first electric motor provided on said second holder, and a roller arranged in contact with said first holder and rotated by said first electric motor for rotating said first holder relative to said second holder, and means for pivoting or inclining said first holder relative to said second holder.

13. The ultrasonic probe apparatus of claim 12, wherein said first electric motor rotates said first holder within an angular range between +90 and −90 degrees.

14. The ultrasonic probe apparatus of claim 13, wherein said pivoting means comprises at least one second electric motor provided on said second holder, and at least one movable member movable in and out by said second electric motor in a radial direction perpendicular to an axis of said second holder, in which said first holder being adapted to be pivotally inclined with respect to said second holder when said movable member is brought into contact with said first holder.

15. The ultrasonic probe apparatus of claim 14, wherein said pivoting means comprises three sets of second electric motors and movable members which are respectively arranged at constant angular intervals along a circumferential direction of said second holder.

16. An ultrasonic probe apparatus comprising:
an ultrasonic probe provided with a phased array transducer for transmitting and receiving ultrasonic waves;
means for supporting said ultrasonic probe pivotally and rotationally;
means for holding said supporting means which supports said ultrasonic probe on a surface of an object to be examined so that ultrasonic beams transmitted from the transducer of the probe are directed to a region to be diagnosed,
said holding means including a plurality of elongated holding legs attached to said supporting means so as to extend therefrom radially and outwardly with respect to a rotation axis of the probe in direct contact with the body surface, each holding leg adapted to be freely deformable to conform with a figure of the object to be examined and further retainable in the deformed state;
fixing means such as adhesive tape for attaching the holding legs directly to the body surface so that said probe is held against the body surface irrespective of the figure of the object to be examined, the ultrasonic beams of said probe directed to the region to be diagnosed by appropriately deforming the holding legs so as to meet with the figure of the object to be examined; and
means for shifting said ultrasonic probe in any desired direction by remote control under the condition that said ultrasonic probe is held on the surface of the object to be examined by said holding means.

17. The ultrasonic probe apparatus of claim 16, wherein said supporting member comprises a first holder for supporting said ultrasonic probe therewithin, and a second holder for rotatably and pivotally supporting said first holder.

18. The ultrasonic probe apparatus of claim 17, wherein said ultrasonic probe shifting means comprises means for rotating said first holder relative to said second holder, and means for pivoting said first holder relative to said second holder.

19. An ultrasonic probe apparatus comprising:
an ultrasonic probe provided with a phased array transducer for transmitting and receiving ultrasonic waves;
means for supporting said ultrasonic probe pivotally and rotationally including a first holder for supporting said ultrasonic probe therewithin, and a second holder for rotatably and pivotally supporting said first holder;
means for holding said supporting means which supports said ultrasonic probe on a surface of an object to be examined; and
means for shifting said ultrasonic probe in any desired direction by remote control under the condition that said ultrasonic probe is held on the surface of the object to be examined by said holding means, said shifting means including a first electric motor provided on said second holder, and a roller arranged in contact with said first holder and rotated by said first electric motor for rotating said first holder relative to said second holder, and means for pivoting said first holder relative to said second holder.

20. The ultrasonic probe apparatus of claim 19, wherein said first electric motor rotates said first holder within an angular range between +90 and −90 degrees.

21. The ultrasonic probe apparatus of claim 20, wherein said pivoting means comprises at least one second electric motor provided on said second holder, and at least one movable member movable in and out by said second electric motor in a radial direction perpendicular to an axis of said second holder, in which said first holder being adapted to be pivotally inclined relative to said second holder when said movable member is brought into contact with said first holder.

22. The ultrasonic probe apparatus of claim 21, wherein said pivoting means comprises three sets of second electric motors and movable members which are respectively arranged at constant angular intervals along a circumferential direction of said second holder.

23. An ultrasonic probe apparatus comprising:
an ultrasonic probe provided with a transducer for transmitting and receiving ultrasonic waves;
means for supporting said ultrasonic probe rotationally and pivotally, said supporting means including a first holder for supporting said ultrasonic probe therewithin, and a second holder for rotationally and pivotally supporting said first holder;
means for holding said supporting means which supports said ultrasonic probe on a surface of an object to be examined in such a manner that ultrasonic beams transmitted from the transducer of the probe are directed to a region to be diagnosed, said holding means including a plurality of holding legs provided on said supporting means so as to extend therefrom radially and outwardly with respect to the rotation axis of the probe in direct contact with the surface, said holding legs being adapted to be freely deformable according to a figure of the object to be examined and retainable in the deformed state,
said holding legs adapted to be attached to the body surface with fixing means such as an adhesive tape, whereby said probe can be retained against varying body surface shapes, the ultrasonic beams transmitted from the transducer of said probe thereby directed to the region to be diagnosed by appropriately deforming the holding legs to meet with the body surface shape of the object to be examined; and
means for changing the direction of the ultrasonic probe in any desired direction by remote control under the condition that said probe is held on the surface of the object to be examined, said direction changing means including means for rotating said first holder relative to said second holder, and means for pivotally inclining said first holder relative to said second holder.

24. An ultrasonic probe holding apparatus comprising:
means for supporting an ultrasonic probe provided with a transducer for transmitting and receiving ultrasonic waves rotationally and pivotally; and
means for holding said supporting means on a surface of an object to be examined, said holding means including a plurality of holding legs each extending from the supporting means to an end section in an initial configuration so as to extend therefrom radially and outwardly with respect to the rotation axis of the probe and adapted so that each end section lies fiat in direct contact with the body surface,
said holding legs being adapted to be freely deformable according to a profile of the object to be examined and further retainable in the deformed state while at the same time retaining shape memory of the initial holding leg configuration whereby said support means are held onto variable body surface shapes of the object to be examined, the probe directed to the region to be diagnosed by appropriately deforming the holding legs so as to conform with the profile of the object to be examined.

25. The ultrasonic probe holding apparatus of claim 24, wherein said supporting means comprises a first holder for holding the ultrasonic probe therewithin, and a second holder for pivotally holding said first holder, in which further comprises means for shifting said first holder in any desired directions by remote control under the condition that the ultrasonic probe is held on the surface of the object to be examined, said shifting means including means for rotating the first holder relative to said second holder, and means for pivotally inclining said first holder relative to said second holder.

* * * * *

UNITED STATES PATENT AND TRADEMARK OFFICE
CERTIFICATE OF CORRECTION

PATENT NO. : 5,381,794
DATED : January 17, 1995
INVENTOR(S) : Tei et al.

It is certified that error appears in the above-indentified patent and that said Letters Patent is hereby corrected as shown below:

Column 2, line 6, change "testing, is" to --testing, it is--;

Column 2, line 43, change "off" to --of--;

Column 7, line 14, change "oil" to --on--;

Column 9, line 5, change "ease" to --case--;

Column 12, Claim 8, line 64, change "fiat" to --flat--;

Column 16, Claim 24, line 16, change "fiat" to --flat--.

Signed and Sealed this

Twenty-ninth Day of April, 1997

Attest:

BRUCE LEHMAN

Attesting Officer

Commissioner of Patents and Trademarks